(12) United States Patent
Bernstein et al.

(10) Patent No.: US 11,185,569 B2
(45) Date of Patent: Nov. 30, 2021

(54) ACTRIIB:FC TO TREAT INFERTILITY IN FEMALES

(71) Applicant: University Of Cincinnati, Cincinnati, OH (US)

(72) Inventors: Lori R. Bernstein, Montgomery Village, MD (US); Tom Thompson, Loveland, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 16/098,221

(22) PCT Filed: May 4, 2017

(86) PCT No.: PCT/US2017/031054
§ 371 (c)(1),
(2) Date: Nov. 1, 2018

(87) PCT Pub. No.: WO2017/192847
PCT Pub. Date: Nov. 9, 2017

(65) Prior Publication Data
US 2019/0160144 A1      May 30, 2019

Related U.S. Application Data

(60) Provisional application No. 62/331,658, filed on May 4, 2016.

(51) Int. Cl.
| A61K 38/17 | (2006.01) |
| A61P 15/08 | (2006.01) |
| A61K 38/24 | (2006.01) |
| A61K 47/68 | (2017.01) |
| A61K 31/57 | (2006.01) |

(52) U.S. Cl.
CPC ............ *A61K 38/179* (2013.01); *A61K 31/57* (2013.01); *A61K 38/24* (2013.01); *A61K 47/68* (2017.08); *A61P 15/08* (2018.01); *C07K 2319/30* (2013.01)

(58) Field of Classification Search
None
See application file for complete search history.

(56) References Cited

U.S. PATENT DOCUMENTS

| 2009/0075380 A1 | 3/2009 | Smith et al. | |
| 2010/0048525 A1* | 2/2010 | Gleicher | A61K 31/5685 514/178 |
| 2010/0316644 A1 | 12/2010 | Seehra et al. | |
| 2012/0046228 A1 | 2/2012 | Molina | |
| 2017/0190774 A1* | 7/2017 | Kara | A61P 43/00 |
| 2017/0227554 A1* | 8/2017 | Gleicher | G01N 33/74 |

FOREIGN PATENT DOCUMENTS

| EP | 2475427 | * | 3/2011 | ............. A61P 19/08 |
| WO | 2003/006057 A1 | | 1/2003 | |
| WO | WO 03/022303 | * | 3/2003 | ............. A61K 38/24 |
| WO | WO 2004/056780 | * | 7/2004 | ............. C07D 215/38 |
| WO | 2008/140794 A1 | | 11/2008 | |

OTHER PUBLICATIONS

Padma Rekha Jirge, J Hum Reprod Sci. 2016; 9: 63-69 (Year: 2016).*
Pirollo et al., Cancer Res. 2008; 68(5): 1247-1250 (Year: 2008).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
Chen et al., www.moleculartherapy.org vol. 23 No. 3, 434-444 Mar. 2015 (Year: 2015).*
Homburg et al., Fertil. Steril. 1993, 59: 527-531 (Year: 1993).*
Griffin and Mellon, Endocrinology 142(11):4617-4622 (Year: 2001).*
Bernstein et al., Fertility and Sterility, (Sep. 2015) vol. 104, No. 3, Suppl. 1, pp. e63. Abstract No. O-161 (Year: 2015).*
Fujioka et al., Am J Physiol Endocrinol Metab, 2012; 302: E694-E704 (Year: 2012).*
Bernstein, LR et al., Activin Decoy Receptor ActRIIB:Fc Lowers FSH and Therapeutically Restores Oocyte Yield. Prevents Oocyte Chromosome Misalignments and Spindle Aberrations, and Increases Fertility in Midlife Female SAMP8 Mice, Endocrinology, vol. 157, No. 3, Mar. 2016, pp. 1234-1247.
Sharara et al., The detection of diminished ovarian reserve in infertile women, American Journal of Obstetrics & Gyneco, Mosby, St. Louise, MO, US, vol. 179, No. 3, Sep. 1, 1998, pp. 804-812.
European Patent Office, International Search Report and Written Opinion issued in corresponding PCT Application No. PCT/US2017/031054, dated Jul. 24, 2017 (14 pages).

* cited by examiner

*Primary Examiner* — Christina M Borgeest
(74) *Attorney, Agent, or Firm* — Wood Herron & Evans LLP (57) ABSTRACT

Described are novel female fertility therapies. A first aspect of the invention is directed to therapies that include FSH lowering methodologies to prevent and/or treat egg infertility. A second aspect of the invention is directed to agents that bind to activin, bind to receptors that bind activin, or that otherwise disrupt activin signaling (collectively referred to herein as "activin pathway modifier agents" or "APM agents") and methods of utilizing these agents to prevent and/or treat egg infertility. A third aspect of the invention is directed to methods of administering an effective amount of an APM agent to a subject to increase oocyte yield and/or ovarian reserve. All three aspects of the invention may be used in humans and in animals. Additional aspects of the invention include therapeutic drug kits for treatment of humans and animals based on the methodologies described above.

12 Claims, 4 Drawing Sheets

ACTRIIB:FC TO TREAT INFERTILITY IN FEMALES

CROSS-REFERENCE TO RELATED APPLICATIONS

This application is a national stage application under 35 U.S.C. § 371 of International Application No. PCT/US2017/031054, filed on May 4, 2017, which claims priority to U.S. Provisional Application No. 62/331,658 filed May 4, 2016, the disclosures of which are hereby incorporated by reference herein in their entireties.

FIELD

The present invention is directed to new female fertility therapies and associated kits.

BACKGROUND

Rates of infertility, miscarriage, and trisomic pregnancies increase dramatically in women as they age, and currently there is no cure. For many advanced maternal age women (AMA, ≥35 years old) there is increased risk of oocyte, embryonic and fetal aneuploidy; infertility due to advanced maternal age, diminished ovarian reserve, recurrent implantation failure; premature ovarian failure, elevated estradiol, prior miscarriages, and/or prior aneuploid conceptuses including trisomic pregnancies and births including Down syndrome, Patau syndrome, and Edward syndrome that lead to profound disabilities and early death. These problems are collectively referred to as "egg infertility." Egg infertility increases exponentially with age. The root cause of egg infertility is a dramatic increase in the rates of chromosome segregation errors in the oocyte. Egg infertility is a significant public health problem, with 1 in 5 US women now attempting her first pregnancy after the age of 35. By age 42, up to 87% of embryos are aneuploid and 40-50% of women experience miscarriages and infertility.

Several hundred thousand women in the US and 1.2 million women throughout the developed world suffer from egg infertility each year and are unable to have a baby because they cannot conceive or maintain a pregnancy. Others afflicted with egg infertility have babies with devastating trisomic diseases such as Down syndrome. A therapy for couples afflicted with egg infertility would be profoundly useful by preventing infertility, miscarriages, Down syndrome, and other trisomies. There is a need for therapies that prevent or treat egg infertility.

Primates, prize farm animals, and racing horses with declining fertility also undergo assisted reproductive technologies, including intrauterine insemination ("IUI") and in vitro fertilization ("IVF"). Some species experience egg infertility with maternal age. Presently, there are no methods for preventing and/or treating egg infertility in animals.

Each year well over a million women throughout the US and the world undergo ovarian stimulation with FSH medications to induce the growth of multiple eggs for ovulation. Aromatase inhibitors to induce ovulation by increasing endogenous levels of FSH are an alternative therapy used for some infertility patients. Patients who undergo these stimulation regimens include women undergoing IUI and women undergoing IVF. They also include women seeking to have a baby with their own eggs and women serving as donors of their eggs. There is a need for therapies that increase oocyte yield and/or ovarian reserve to improve assisted reproduction technologies.

New therapeutic alternatives to FSH administration to increase oocyte yield and/or ovarian reserve in assisted reproductive technologies would be generally useful for women undergoing assisted reproduction. Such therapeutic alternatives would be especially useful for women with a poor response to FSH stimulation, which includes women with high FSH, high estradiol (E2), and diminished ovarian reserve ("DOR"). These women generally show a poor response to ovarian stimulation regimens that employ high FSH. Therapies to increase oocyte yield and/or ovarian reserve would also be useful in animals.

As women age, serum FSH becomes elevated throughout the menstrual cycle. From the mid-30s to the early 40s, high FSH occurs in the context of regular cycles and the diminution of fertility that occurs prior to the premenopausal onset of irregular cyclicity. Since FSH mediates the process by which oocytes prepare for meiotic chromosome segregation, FSH may play a role in regulating fidelity of chromosome segregation. However, for many years, OB/Gyn physicians have regarded high FSH as an epiphenomenon of ovarian aging that is not a cause of egg infertility. Instead, ovarian aging processes inherent within the oocyte that cause molecular damage to the chromosome segregation apparatus were deemed as the root cause of egg infertility. Accordingly, most physicians regard high FSH as associated with, but not causative of ovarian aging.

BRIEF DESCRIPTION OF THE DRAWINGS

The drawing referenced herein form a part of the specification.

SUMMARY

Described herein are novel female fertility therapies. A first aspect of the invention is directed to therapies that include FSH lowering methodologies to prevent and/or treat oocyte, embryo and fetal aneuploidy, female infertility due to advanced maternal age, diminished ovarian reserve, premature ovarian failure, and/or recurrent implantation failure, miscarriages, and trisomic pregnancies (collectively referred to herein as "egg infertility."). A second aspect of the invention is directed to agents that bind to activin, bind to receptors that bind activin, or that otherwise disrupt activin signaling (collectively referred to herein as "activin pathway modifier agents", "APM agents") and methods utilizing these agents to prevent and/or treat egg infertility. A third aspect of the invention is directed to methods of administering an effective amount of an APM agent to a subject to increase oocyte yield and/or ovarian reserve, which may be used with assisted reproductive technologies to treat female infertility with an APM agent. All three aspects of the invention may be used in human subjects and in animal subjects. Additional aspects of the invention include therapeutic drug kits for treatment of humans and animals based on the methodologies described above.

DETAILED DESCRIPTION

Described herein are novel female fertility therapies. A first aspect of the invention is directed to therapies that include follicle-stimulating hormone ("FSH") lowering methodologies to prevent and/or treat oocyte and embryo aneuploidy, infertility, miscarriages, and trisomic pregnancies (collectively referred to herein as "egg infertility"). A second aspect of the invention is directed to agents that bind to activin, bind to receptors that bind activin, or that otherwise disrupt activin signaling (collectively referred to herein as "activin pathway modifier agents", "APM agents") which are utilized to prevent and/or treat egg infertility. A third aspect of the invention is directed to methods of administering an effective amount of an APM agent to a subject to increase oocyte yield and/or ovarian reserve, which may be used with assisted reproductive technologies to treat female infertility. All three aspects of the invention may be used in human subjects and in animal subjects. Additional aspects of the invention include therapeutic kits comprised of FSH lowering medications or comprised of APM agents, to treat subjects, including human subjects and animal subjects. Embodiments of the kits contain the medications in an easy to use format for administration based on the methodologies described herein. These medications include FSH lowering agents and/or APM agents and may also include adjunct medications such as luteinizing hormone ("LH") and/or human chorionic gonadotropin ("hCG") or a gonadotropin releasing hormone analogs to trigger ovulation; aromatase inhibitors; and progesterone, estrogen, and testosterone and their pharmaceutically acceptable derivatives.

An embodiment of the invention is directed to methods of treating or preventing egg infertility employing agents that lower FSH. Another embodiment of the invention is directed to methods of treating or preventing egg infertility employing APM agents. Some agents useful in embodiments of the invention include both FSH lowering and APM properties, although others either have FSH lowering properties or APM properties. Methods employing FSH-lowering agents and APM agents may also be considered individually because modification of activin pathway activities by APM agents may exert their therapeutic effects by means that are at least in part separable from their FSH-lowering properties.

In embodiments of the invention, the FSH lowering agents, APM agents, or both the FSH lowering agents and the APM agents may be used to treat subjects (including human subjects and animal subjects) to accomplish at least one of the following two goals:

(1) Prevent oocyte, embryo, and fetal aneuploidy. This includes oocyte, embryonic, and fetal aneuploidy in subjects with diminished ovarian reserve, high FSH levels, elevated estradiol levels, recurrent implantation failure, premature ovarian failure, prior miscarriages, and prior aneuploid conceptuses including trisomic pregnancies and births.

(2) Prevent and/or treat infertility and increase fertility. This includes subjects with diminished ovarian reserve, high FSH levels, elevated estradiol levels, recurrent implantation failure, premature ovarian failure, prior miscarriages, and prior aneuploid conceptuses including trisomic pregnancies and births.

Another embodiment of the invention is directed to the use of an APM agent to increase oocyte yield and/or ovarian reserve, which may be useful in facilitating assisted reproductive technologies, such as IUI and IVF in humans and animals.

The methods described herein include the steps of administering an effective amount of a FSH lowering agent and/or an APM agent to a female subject for at least a portion of at least one reproductive cycle, and in some embodiments, for at least one complete reproductive cycle, prior to attempting conception.

Alternatively, the FSH-lowering agents and/or APM agents are administered to the subject for two or more cycles or a portion of two or more cycles, with the pregnancy attempt avoided until the end of the final cycle of treatment. This is done so that poor quality eggs are eliminated and the "ideal" egg that has been nurtured to grow in a young microenvironment is the egg with which pregnancy is attempted.

In other embodiments, the FSH-lowering agents and/or the APM agents may also be administered to the subject for the period of egg growth (several menstrual or estrous cycles prior to ovulation in humans and animals, respectively), again with the subject avoiding pregnancy until the final cycle of treatment. The exemplary APM agent ActRIIB:Fc is effective in preventing egg aneuploidy and increasing fertility when administered for the duration of the window of egg growth. The basis for therapeutic activity of APM agents is not necessarily based on FSH-lowering properties that many of them may work, in theory, by an independent mechanism.

The same methodologies (above) apply to both FSH lowering agents and APM agents and that it is intended for the methods to induce the growth of multiple follicles as well as for the prevention of egg aneuploidy and infertility.

An alternative method of FSH lowering utilizes the administration of a gonadotropin releasing hormone antagonist. Exemplary gonadotropin releasing hormone antagonist(s) ("GnRHant") include cetrorelix, ganirelix, abarelix, elagolix, and/or degarelix. In embodiments of the invention, one or more GnRHants are administered along with low dose LH activity (LH or hCG) and a surge dose of LH activity in the peri-ovulatory period; but no FSH is needed. This is because GnRHants partially lower FSH while strongly suppressing LH. Administering GnRH analog with LH activity will normalize FSH through the cycles of treatment. In embodiments of this alternative, the treatment is conducted for at least two cycles, in both the follicular and luteal phases, prior to the pregnancy attempt, as described above.

In embodiments of the invention, the FSH lowering agent, the APM agent, or combinations thereof, are administered at a dose effective to provide sustained suppression of FSH for several weeks of treatment while not suppressing FSH menstrual cycling in the subject. In other words, the dose of the FSH lowering agent, the APM agent, or combinations thereof is administered in an amount effective to result in the desired outcome, i.e., at least one of treating egg infertility, preventing egg infertility, or to increase oocyte yield and/or ovarian reserve, while maintaining cyclicity in the subject during the period of treatment. Depending on the metabolic rate of the FSH lowering agent, the APM agent, or combinations thereof in the subject, dose of the agent or agents may need to be repeatedly administered so that the serum levels necessary to obtained the desired result is maintained for the desired duration.

Another aspect of the invention is directed to kits for treating female infertility. An embodiment of a kit contains medications that lower FSH in a formulation and combination to prevent and treat egg infertility. Another embodiment of the kit contains APM agents in a formulation and combination to prevent and treat egg infertility. Another embodiment of the kit contains APM agents in a formulation to induce the growth of multiple follicles and increase oocyte production for use with assisted reproduction methods. Some embodiments of the kits may be used to treat human subjects and other embodiments may be used to treat animal subjects. Some embodiments of these kits may also include adjunct medications such as LH, hCG, estrogen, progesterone, and/or testosterone or their derivatives, aromatase inhibitor, and/or a GnRH analog to induce ovulation and support reproductive function.

Patient compliance and therapeutic success of treatments with FSH-lowering drugs and APM agents will be facilitated by drugs provided in a kit format that simplifies the therapeutic regimen for the human subject. Kits will also facilitate drug administration for animal owners and caretakers in a setting such as a farm or zoo location. It will be appreciated that kits with different concentrations of medications and durations of therapeutic treatment are formulated to be physiologically applicable to the animal species for which the treatments are intended.

An embodiment of the kit includes doses of FSH-lowering agents and/or APM agents necessary to implement the treatments described herein. The kits may include LH, hCG, or GnRH agonist to induce ovulation, and may optionally include the medical instruments, such syringes, necessary to administer the doses as well as instructions for administering the doses.

The use of FSH-lowering agents and of APM agents to prevent oocyte and embryo aneuploidy to treat and prevent female infertility, miscarriages and trisomic births due to aneuploidy, and to increase oocyte and/or ovarian reserve, and embryo yield has not been previously described in the literature.

In embodiments of the invention, the APM agent is ActRIIB:Fc. ActRIIB is a transmembrane receptor for activin. ActRIIB:Fc (aliases include ACE-031 and ACVR2B) is a cloned soluble chimera of ActRIIB that has the extracellular domain, lacks the transmembrane and cytoplasmic kinase domains, and is fused to an IgG Fc sequence. ActRIIB:Fc is an activin decoy receptor that sequesters activin and inactivates activin signaling. In embodiments of the invention, ActRIIB:Fc, or derivatives thereof which may include amino acid deletions or substitutions that do not negatively affect activin binding, is administered at a dose effective to provide sustained suppression of FSH for several weeks of treatment while not suppressing FSH menstrual cycling in the subject. In other words, the dose of ActRIIB:Fc is administered in an amount effective to result in the desired outcome, i.e., at least one of treating egg infertility, preventing egg infertility, or to increase oocyte yield and/or ovarian reserve, while maintaining cyclicity in the subject during the period of treatment. In embodiments, the dosage is given at a dose to maintain serum levels of ActRIIB:Fc between 4 mg/kg and 10 mg/kg, such as 7 mg/kg, plus or minus 1 mg/kg. Accordingly, depending on the metabolic rate of ActRIIB:Fc in the subject, ActRIIB:Fc may need to be repeatedly administered so that the serum levels necessary to obtain the desired result is maintained for the desired duration.

Conventional paradigms in the field point away from FSH as a cause of aneuploidy and instead implicate molecular damage to the egg and the follicle accumulated over many years. The conventional thought in the OB/Gyn field is that the egg itself becomes old due to molecular damage that inherently occurs during the process of aging. These degenerative processes include cohesin defects, telomere shortening, mitochondrial damage, reactive oxygen species (ROS), and spindle defects. The current thinking is that this damage takes years to accumulate and cannot be reversed by a short term clinical treatment of the patient. The notion that preventable mechanisms contribute to oocyte aneuploidy has not been previously appreciated by those in the field, and treatment of oocyte aneuploidy was even considered to be impossible. Thus, therapies employing FSH lowering agents and APM agents have not previously been considered.

Examples of FSH-lowering agents and of APM agents to treat egg infertility are listed in Table 1. The same APM agents listed in the right column may also be used to increase oocyte and/or ovarian reserve for assisted reproductive technologies.

| FSH lowering agents and other FSH pathway inhibitors | Activin pathway modifier agents (APM agents) |
|---|---|
| FSH beta chain peptides (e.g., aa90-95; 81-95; 33-53) | ActRIIB:Fc (ACE-031) and derivative agents |
| FSH receptor peptides (e.g., as 551-555; 533-555; 650-653; 649-653) | ActRIIA:Fc (ACE-011; sotatercept) and derivative agents; TGFI3 antagonists with altered ligand specificities toward activin ligands (PRDC, gremlin, chordin, noggin, etc. ) |
| Cetrorelix, Ganirelix, Abarelix, Elagolix, and/or Degarelix GnRH antagonist to partially suppress FSH throughout treatment; plus low dose LH activity (LH or hCG); ovulation induction with LH or hCG, for two or more cycles of treatment, where pregnancy is avoided until the last cycle of treatment. | Follistatin, including splice variants 288 and 315 and derivative agents (e.g., with or without fusion Fc regions, domain modifications or deletions) |
| Anti FSH antibodies | |
| Inhibins A, B | FSTL3 and derivative agents |
| | BYM338 and derivative agents; other inhibitors of Type II activin receptors including anti-activin-receptor antibodies and derivative agents; Activin receptor binding activin peptides and related agents with dominant negative effect on activin receptor signaling |
| Follistatin, including splice variants 288 and 315 and derivative agents (e.g., with or without fusion Fc regions, domain modifications or deletions) | ACE-083 and derivative agents |
| ActRIIB:Fc (ACE-031) | |
| | Antibodies or other engineered agents (e.g. camelids, adnectins) directed to bind and antagonize Activin A, B and/or AB |
| ActRIIA:Fc (ACE-011) | ALK4/5/7 kinase inhibitors (e.g., SB431542, LY-2157299) |
| 313-hydroxy-4-pregnen-20-one (3HP), | Myostatin |
| 313-hydroxy-4-pregnen-20-one-3-acetate (3HPA) | Dominant negative Activins or Decoy Ligands, including dominant negatives and decoys of Activin A, Activin B, Myostatin, GDF11, |

| FSH lowering agents and other FSH pathway inhibitors | Activin pathway modifier agents (APM agents) |
|---|---|
| RNA interference towards FSH, FSH receptor<br>Anti-MCillerian Hormone (AMH)—alias Mallerian-inhibiting substance | Nodal agents that cannot signal but still bind receptors. Activin peptide antagonists.<br>Cerberus<br>RNA interference directed towards ActrIIA, ActrIIB, ALK4, Smad2 Smad 3, Activin A or Activin B<br>Modified Activin pro-domain |

EXAMPLE 1

Materials and Methods

SAM P8 mouse colony. Mice were housed and bred in-house at the University of Maryland School of Medicine (UM) animal facility in Baltimore and cared for according to the National Academy of Sciences guidelines for compassionate use and care of laboratory animals, using UM Institutional Animal Care and Use Committee ("IACUC")-approved animal use protocols as described. Prior to the period before their use in experiments, female mice were housed at a density of 3-5 mice/cage. The presence of male cages and the housing of females in open cages accessible to male smell with a low density of females per cage are needed to achieve regular cyclicity of the SAMP8 female mice in the colony. Three or more weeks before blood draws or oocyte retrievals, female mice were housed in a room that contained open air cages containing 2 mice per cage. Cages containing 3-5 intact males per cage (aged 2-9 months) were interspersed with cages containing female mice, in a 1:3 ratio of male to female cages. These conditions promote regular cyclicity in the SAMP8 female mice.

Experimental bleeds, serum preparation, and quantization of serum FSH levels. Survival bleeds and terminal bleeds, preparation of mouse sera, and quantization of serum concentrations of FSH with a Milliplex MAP Rat Pituitary magnetic bead panel (RPTGMAG-86K; Millipore) were performed as according to manufacturer's instructions. Standard pooled sera from ovariectomized rats were included alongside test samples to normalize measurements between assays and to assess intra- and inter-assay variability. Duplicate FSH measurements were performed for each mouse sample as described.

Purification of ActRIIB:Fc. ActRIIB:Fc was expressed in Chinese hamster ovary cells and purified from conditioned media as described.

Ovariectomy of female SAMP8 mice, and treatment of ovariectomized mice with ActRIIB:Fc with several ActRIIB:Fc dosages. Eighteen SAMP8 female mice aged 7.4-7.6 months were ovariectomized according to standard methods. Mice were permitted to recover for 2.3 weeks before commencement of injections. Mice aged 8.2-8.5 months were injected subcutaneously (sc) with 0.1 ml of sterile PBS saline solution. Survival bleeds were then performed for control FSH measurements prior to ActRIIB:Fc injection.

Mice were then divided into two test groups comprised of 9 mice per group. Mice were injected sc with sterile PBS containing ActRIIB:Fc. One test group received 4 mg/kg ActRIIB:Fc, and the other test group received 10 mg/kg ActRIIB:Fc. Survival bleeds were performed for both test groups 24 hours and 96 hours after ActRIIB:Fc injection. Blood sera were prepared and FSH levels were analyzed as described above.

Identification of estrous cycle days and estrous cycle lengths in cycling mice by vaginal cytological analyses. Vaginal smearing was performed to obtain cells for staining and cytological analyses. Smearing and histological analyses stained smears was performed as described.

Treatment of cycling mice with control saline and ActRIIB:Fc and collection of blood sera for FSH measurements. Mice at a mean age of 5.92 months of age (ranging from 5.6 to 6.2 months) were injected subcutaneously with PBS (vehicle control). Blood was collected as survival bleeds on the next morning of estrus 1-4 days after the PBS injection, and processed to generate serum according to methods described.

ActRIIB:Fc in PBS was injected subcutaneously into regularly cycling SAMP8 female mice ranging from 5.99 to 6.35 months at a dosage of 7 mg/kg. Blood was drawn 1-4 days later and processed to generate serum samples on the next morning of estrus.

ActRIIB:Fc boosters were continued every 3-4 days after the initial injection. The dosage of ActRIIB:Fc in the booster shots was designed to supplement the ActRIIB:Fc remaining in the bloodstream to restore a serum ActRIIB:Fc concentration of 7 mg/kg. The amount of ActRIIB:Fc remaining in the bloodstream several days after the ActRIIB:Fc injection was calculated using the equation for exponential decay, $$A = A_o e^{-t/T}$$

where t is the time elapsed since the prior injection (3 days or 4 days); A=the final serum concentration after the elapsed time t since the prior injection; $A_o$=7 mg/kg ActRIIB:Fc (initial serum concentration of ActRIIB:Fc at the time of the first injection); and T=15.87, the constant for exponential decay for ActRIIB:Fc. This constant was calculated based on assuming an 11 day half-life of ActRIIB:Fc in mice. The booster dose of ActRIIB:Fc was computed as 7 mg/kg minus A, where A is the dose in mg/kg of ActRIIB:Fc remaining after the decay.

ActRIIB:Fc treatments were continued every 3-4 days using this method for calculating booster dosage to reconstitute the initial administered dosage until approximately 3 weeks of treatment had been given, after which a final terminal bleed was taken on the morning of estrus, usually the morning that oocytes were collected from the mice at approximately 6.4 months of age (age range of 6.2-6.6 months). Terminal blood collections were performed according to standard methods.

Gonadotropin measurements in cycling SAMP8 mice—Duplicate FSH measurements were performed for each mouse serum sample. To assess FSH suppression, FSH levels were compared on the same cycle day of the estrus cycle between serum samples of mice that had been administered vehicle vs. ActRIIB:Fc. Number of mice: vehicle control: 10; ActRIIB:Fc treated 1-4 days: 20 mice; ActRIIB:Fc treated for 19-24 days: 9 mice.

Oocyte collection, processing and analyses. Oocytes were collected from cycling SAMP8 female mice, processed, analyzed for morphology, fixed, and stained according to standard methods. Mice were smeared to characterize their estrous cycles. Mice were injected IP with 5 IU hCG on the afternoon of proestrus to induce synchronous ovulation for the mice undergoing oocyte retrievals. Oocytes were collected 14 to 16 hours after hCG administration, and were denuded of granulosa cells utilizing standard methods. Scoring of oocyte morphology, removal of the zona pellucida, fixation, immunofluorescent staining, and scoring of chromosome misalignments and spindle aberrations were performed.

Analyses of SAMP8 litter sizes after treatment with ActRIIB:Fc. Intact female SAMP8 mice aged 5.5-6 months were injected intraperitoneally (ip) with ActRIIB:Fc at a dose of 7 mg/kg. This was followed by booster injections of ActRIIB:Fc administered every 3-4 days to maintain the initial administered dose of ActRIIB:Fc for 21-22 days, as described above. On the day that the last injection was administered, the female mice were housed with intact male SAMP8 mice aged 4.75 months for the duration of 11 days. By these means females had the opportunity to experience two evenings of proestrus in two different cycles in which they could get pregnant. Males were then removed from the female cages, and daily checks were initiated 10 days later and continued for an additional 14 days.

Females were approximately 6.2-6.7 months of age at the initiation of pairing with the male, and were 6.9-7.5 months of age at parturition. Pups were counted daily each morning by 10 am. Pups lived for several days with the dam, during which pup viability was assessed. Litter sizes were compared to litter sizes of untreated SAMP8 female mice where the untreated females and the males were of the same age range as the experimental mice.

Results

ActRIIB:Fc suppresses FSH in ovariectomized SAMP8 mice. Mice were injected with ActRIIB:Fc or with saline solution. FSH levels were measured after 24 hours and 96 hours of ActRIIB:Fc treatment for mice injected with ActRIIB:Fc dosages of 4 mg/kg and 10 mg/kg. FSH levels in treated animals were compared to FSH levels in blood sera drawn just before ActRIIB:Fc treatment was initiated. Mean FSH levels prior to treatment were 275,717 pg/ml. FSH levels in mice treated with 4 mg/kg ActRIIB:Fc declined to 94,861, a 65.5% suppression (P <0.0001, two tailed Mann-Whitney Test; Table 2 and FIG. 1).

Mean FSH levels were 156,570 after 96 hours of ActRIIB:Fc treatment (P <0.0001), a 43.2% suppression. These data indicate that ActRIIB:Fc causes FSH suppression that is sustained and also somewhat attenuated such that 66% of the suppression that is achieved at 24 hours was sustained at 96 hours (100×(Untreated−96 hours treated)/(untreated−24 hours treated)=66%). Mice given 10 mg/kg ActRIIB:Fc had 52,628 pg/ml FSH after 24 hours of ActRIIB:Fc treatment, an 80.9% suppression of FSH (P <0.0001 vs. untreated control). Suppression was compared to control untreated values. Therefore FSH suppression by 10 mg/kg of ActRIIB:Fc is 100% sustained for 96 hours of ActRIIB:Fc treatment. P values comparing FSH levels for sera sustained at 96 hours, with mean FSH of 52,144 pg/ml, an 81.1% suppression of FSH from mice before vs. after ActRIIB:Fc treatment for 24 or 96 hours at 4 or 10 mg/kg of ActRIIB:Fc also showed statistically significant differences, with P <0.0001 comparing untreated SAMP8 ovx mice to treated mice at 4 or 10 mg/kg after either 24 or 96 hours of treatment (Table 2). No significant suppression of luteinizing hormone (LH) was detected in mice treated for 24 or 96 hours with 4 mg/kg or 10 mg/kg of ActRIIB:Fc.

| ActRIIB:Fc dosage, mg/kg | ActRIIB:Fc treatment time, hours | Number of mice tested Per group | Mean FSH, pg/ml | SEM, pg/ml | Mean % CV (range) | P vs. un-treated (unpaired) | P vs. Untreated (paired test) | $O_k$ Suppression vs. control |
|---|---|---|---|---|---|---|---|---|
| 0 (control) | NA | 18 | 275,717 | 10,054 | 3.61 (0.06-16.9) | NA | NA | NA |
| 4 | 24 | 9 | 94,861 | 13,376 | 2.84 (2.1-6.5) | <0.0001 | <0.0001 | 65.6% |
|   | 96 | 9 | 156,570 | 10,226 | 2.49 (0.70-5.7) | <0.0001 | 0.0003 | 43.2% |
| 10 | 24 | 9 | 52,628 | 2,886 | 3.43 (0.32-6.7) | <0.0001 | <0.0001 | 80.9% |
|   | 96 | 9 | 52,144 | 9,223 | 4.69 (0-12.5) | <0.0001 | <0.0001 | 81.1% |

Figure 1:
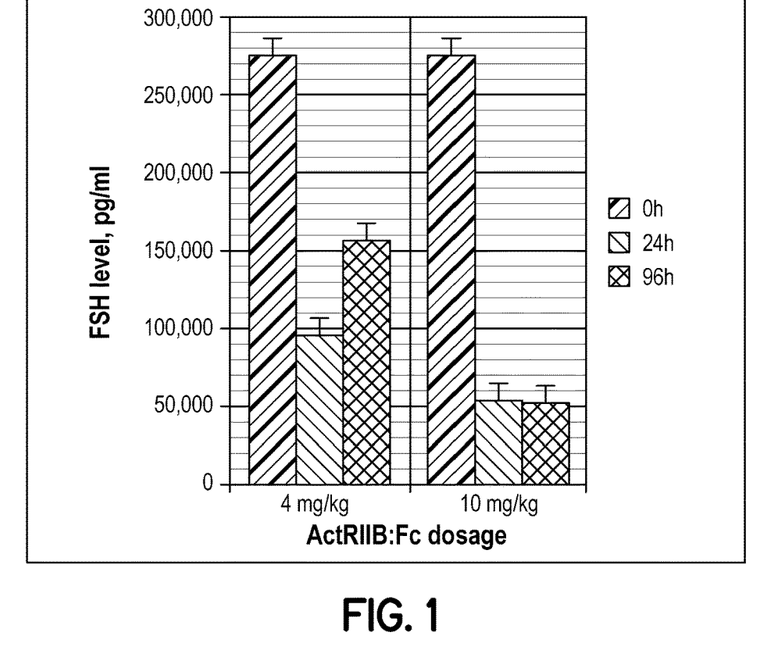
FIG. 1 is a graph of data demonstrating the FSH-lowering effects of ActRIIB:Fc in ovariectomized SAMP8 female mice.

In summary, Table 2 and FIG. 1 demonstrate that ActRIIB:Fc suppresses serum FSH levels in ovariectomized SAMP8 female mice.

ActRIIB:Fc suppresses FSH in cycling midlife female SAMP8 mice. Based on the data from ovariectomized mice it was predicted that a dosage of ActRIIB:Fc that is between 4 and 10 mg/kg such as 7 mg/kg would provide sustained suppression of FSH for several weeks of treatment in cycling mice while not suppressing FSH excessively, so that cyclicity might be maintained in the mice during the period of treatment. Midlife SAMP8 mice ranging from 5.9 to 6.4 months of age were given 7 mg/kg ActRIIB:Fc treatment. ActRIIB:Fc treated mice exhibited a significant suppression of FSH levels on the day of estrus, from a mean of 40,773 pg/ml to a mean of 7,906 pg/ml after 1-4 days of ActRIIB:Fc treatment, a 73.6% inhibition (Table 3 and FIG. 4; P <0.0001).

A test group of SAMP8 mice received booster shots of ActRIIB:Fc every three days. By these means, ActRIIB:Fc levels were maintained between approximately 5.8 to 7 mg/kg for a period of 19 to 24 days. Mice continued to cycle during ActRIIB:Fc treatment. Terminal bleeds were performed on the morning of estrus ("three week treatment test group," 19-24 days after initial ActRIIB:Fc injection depending on when the morning of estrus occurred). SAMP8 mice appeared healthy and showed no signs of pathology in necropsies performed immediately after terminal bleeds were performed. Mice have been treated with 10/mg/kg of ActRIIB:Fc for over a month without toxicity (Lee S J, unpublished data). FSH levels in mice treated with ActRIIB:Fc for 19-24 days were significantly lower than in vehicle-treated mice, with a mean of 40,773 pg/ml in vehicle treated mice, vs. 22,100 pg/ml in ActRIIB:Fc treated mice (Table 3 and FIG. 2; P=0.0002). The percentage suppression for mice treated with ActRIIB:Fc for 19-24 days was 47.3% relative to the vehicle treated mice, less than for 1-4 day treated test group. LH levels were not significantly different between vehicle-treated mice, and mice treated with ActRIIB:Fc.

| ActRIIB:Fc treatment time | Number of mice tested | Mean FSH pg/ml | SEM | Mean % CV (range) | P | % Suppression |
|---|---|---|---|---|---|---|
| 0 (vehicle treated) | 10 | 40,773 | 4,469 | 5.3% (1.31-14.72%) | NA | NA |
| 1-4 days | 20 | 7,906 | 1,778 | 2.1% (0-4.8%) | <0.0001 | 73.6 |
| 19-24 days | 9 | 22,100 | 2,355 | 2.05% (0-4.81%) | 0.0002 | 47.3 |

Figure 2:
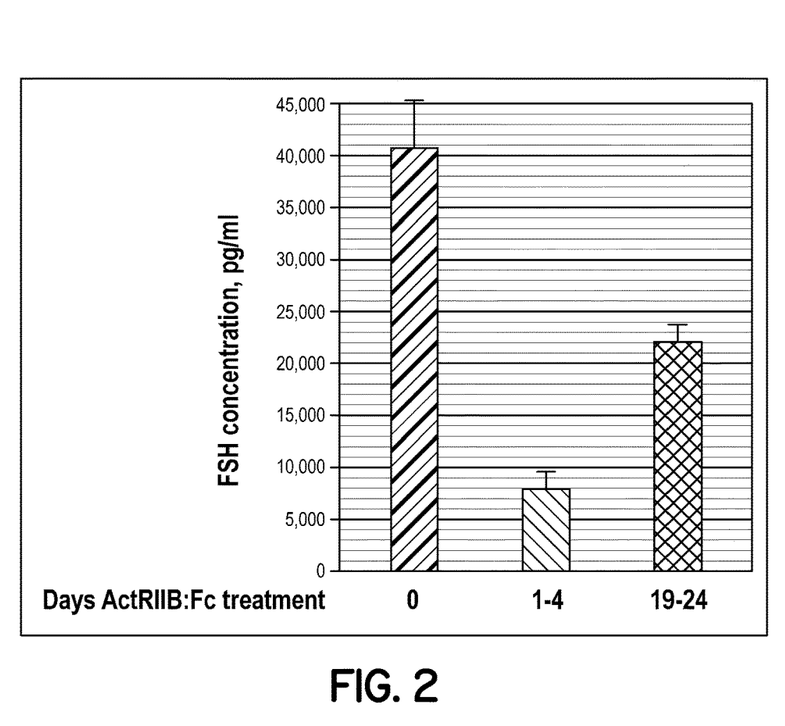
FIG. 2 is a graph of data demonstrating the FSH-lowering effects of ActRIIB:Fc in midlife SAMP8 mice.

In summary, Table 3 and FIG. 2 demonstrate that ActRIIB:Fc suppresses FSH in midlife SAMP8 mice after 1-4 days of treatment and after 19-24 days of treatment.

ActRIIB:Fc increases yield of oocytes and of viable oocytes, and it increases ovarian reserve in midlifeSAMP8 mice to exceed the yields in young SAMP8 mice. Ovulated oocytes were retrieved from the reproductive tracts of SAMP8 mice. Nearly all oocytes recovered were mature eggs that had a polar body. All oocytes were freshly ovulated, with 0/881 of all oocytes exhibiting post-ovulatory aging. No apoptotic oocytes were found in either test group. The yield and viability were compared between oocytes retrieved from young SAMP8 mice aged 2-3 months and midlife SAMP8 mice aged 6.1-8.68 months. A statistically significant decline was observed in mean total oocyte yield per mouse with age, from 12.05 per mouse aged 2-3 months to 11.25 per mouse aged 6-8 months, a decrease of 1.41 oocytes per mouse (P=0.0155, Mann-Whitney test; Table 3, FIG. 3). The mean number of viable oocytes from cumulus-oocyte complexes ("COCs") declined commensurately, from 11.25 per mouse to 9.86 per mouse in the same age groups, a decrease of 1.39 oocytes/mouse (P=0.0119). Almost all oocytes that were not viable were dead, with just 5 of all oocytes recovered that were abnormal due to denudation of cumulus at the time of retrieval (5/881 oocytes). The yield of non-viable and abnormal oocytes (dead or denuded) was 0.8000 non-viable oocytes per mouse from young mice and 0.7727 per mouse for midlife mice (P=0.4174, not significant (NS)). Moreover, 225/241 of oocytes from the young mice were viable oocytes (93.4%), vs. 217/234 from the midlife mice (92.7%; P=0.4648 (NS), Fisher Exact test). These data indicate that the decrease in yield of viable oocytes that occurs with age is attributable to declining yield of total oocytes rather than to declining viability of the oocytes that are ovulated.

The yield of non-viable/abnormal oocytes/mouse was not significantly different between ActRIIB:Fc treated midlife mice and untreated mice (1.6 non-viable oocytes/mouse treated with ActRIIB:Fc vs. 0.7727 non-viable oocytes/untreated mouse, a difference of 0.83/mouse, P=0.2131 (NS)). 191/215 of oocytes from the ActRIIB:Fc-treated midlife mice were viable oocytes (88.8%), vs. 217/234 from the midlife mice (92.7%; P=0.1023 (NS)). These data indicate that the increase in oocyte yield caused by ActRIIB:Fc in midlife mice is predominantly attributable to an increase in the yield of viable oocytes.

The yield of total oocytes in midlife mice treated with ActRIIB:Fc exceeds the yields from untreated young mice by a statistically significant margin, with 14.33 total oocytes per mouse from ActRIIB:Fc treated midlife mice vs. 12.05 per mouse from young mice (2.28 more oocytes per midlife mouse treated with ActRIIB:Fc-treated mouse, P=0.0292). The yield of viable oocytes from ActRIIB:Fc-treated midlife mice also significantly exceeds that from young mice, with 12.73/mouse from ActRIIB:Fc treated mice vs. 11.25/mouse from untreated young mice (1.48 more oocytes per midlife ActRIIB:Fc treated mouse than per young mouse; P=0.0456). The yield of non-viable eggs/mouse is not significantly different between the test groups (1.6/mouse in ActRIIB:Fc treated mice vs. 0.8 in young mice, an increase of 0.80/mouse (P=0.1280, NS), nor is the fraction of viable and non-viable eggs (191/215 (88.8%) viable oocytes/total oocytes for ActRIIB:Fc treated midlife mice vs. 225/241 (83.4%) viable oocytes/total oocytes for young mice; P=0.0619). These data indicate that ActRIIB:Fc administered to midlife mice with declining oocyte yield and viability restores yield of total oocytes and of viable oocytes to levels that are statistically higher than those of young SAMP8 mice.

| Test Group | Midlife | Midlife + ActRIIB:Fc | P | Change In number of eggs after | Young | Midlife | P | Young | Midlife + ActRIIB:Fc | P |
|---|---|---|---|---|---|---|---|---|---|---|
| Total mice (N) | 22 | 15 | — | — | 20 | 22 | | 20 | 15 | |
| Total eggs/mouse | 10.64 | 14.333 | 0.0031 | +3.7 | 12.05 | 10.64 | 0.0155 | 12.05 | 14.333 | 0.0292 |
| Viable eggs/mouse | 9.86 | 12.733 | 0.0051 | +2.9 | 11.25 | 9.86 | 0.0119 | 11.25 | 12.733 | 0.0292 |
| Non-viable eggs/mouse | 0.7727 | 1.60 | 0.2131 | +0.96 | 0.8000 | 0.7727 | 0.4174 | 0.8000 | 1.60 | 0.1280 |
| Fraction of viable eggs (%) | 217/234 (92.7%) | 191/215 (88.8%) | 0.1023 | — | 225/241 (93.4%) | 217/234 (92.7%) | 0.4648 | 225/241 (93.4%) | 191/215 (88.8%) | 0.0619 |
| Fraction of non-viable eggs (%) | 17/234 (7.26%) | 24/215 (11.2%) | 0.1023 | — | 16/241 (6.63%) | 17/234 (7.26%) | 0.4648 | 16/241 (6.63%) | 24/215 (11.2%) | 0.0619 |

Midlife mice were treated with 7 mg/kg of ActRIIB:Fc for approximately 3 weeks (19-24 days). ActRIIB:Fc significantly increased the mean total yield of oocytes in the midlife mice, from 10.64/mouse in untreated midlife mice to 14.33/mouse in ActRIIB:Fc treated midlife mice, an increase of 3.7 oocytes/mouse (34.7% increase, P=0.0031). The yield of viable oocytes increased commensurately, from 9.86/mouse in untreated midlife mice to 12.73 per mouse, an increase of 2.9 oocytes/mouse (29.1% increase, P=0.0051).

Table 4. Illustrates that ActRIIB:Fc treatment of midlife mice increases total yield of oocytes and of viable oocytes, restoring the yield to levels that are significantly greater than those of young SAMP8 mice. Yield of ovulated oocytes was compared between untreated young SAMP8 mice (N=20), untreated midlife mice (N=22), and midlife mice treated with 7 mg/kg dosage of ActRIIB:Fc for approximately 3 weeks (N=15; 19-24 days), with termination of treatment defined by the morning of oocyte recovery. P denotes P values comparing median numbers of oocytes recovered in the various test groups using a Mann-Whitney test. P values and changes in number of eggs after ActRIIB:Fc treatment are shown in bold for sample comparisons that display significant differences.

Figure 3:
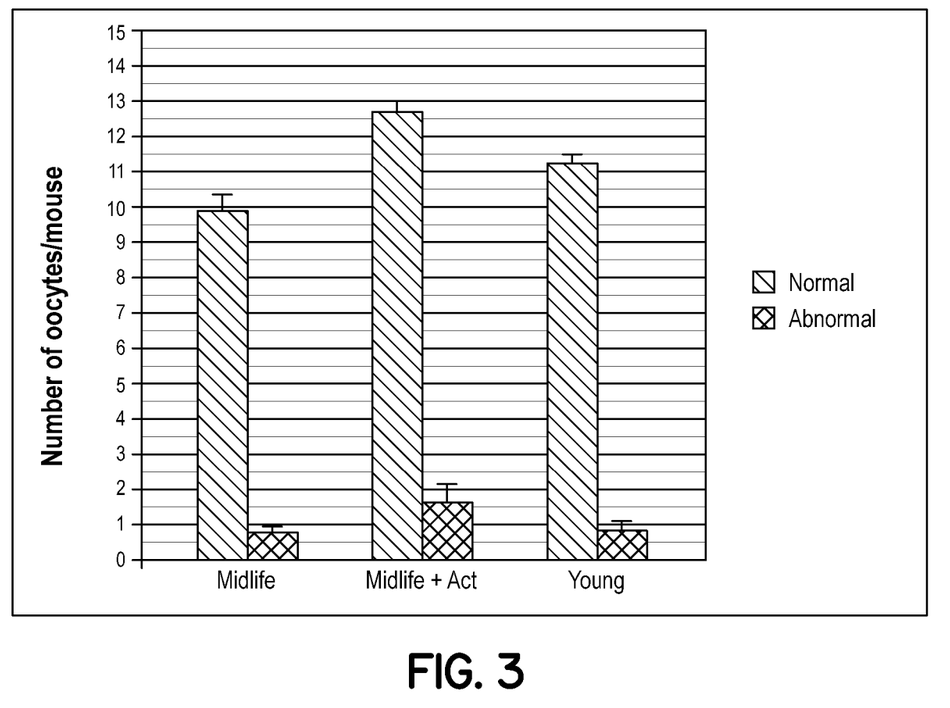
FIG. 3 is a graph of data demonstrating the enhancing effect of ActRIIB:Fc on oocyte yield in midlife SAMP8 mice.

FIG. 3 demonstrates that treatment of midlife SAMP8 female mice with ActRIIB:Fc enhances oocyte yield. Test groups comprised of midlife mice, midlife mice treated with ActRIIB:Fc, and young mice are labeled on the x-axis. Gray bar graphs: Viable oocytes. Black bar graphs: non-viable/abnormal oocytes. ActRIIB:Fc restores the yield of viable oocytes to midlife mice and exceeds the yields of viable oocytes that are recovered from young mice. Error bars are SEM for viable oocytes (Normal) and for non-viable oocytes (Abnormal).

ActRIIB:Fc therapeutically reduces the rates of chromosome misalignments and spindle aberrations in ovulated oocytes from midlife SAMP8 mice.

Figure 4:
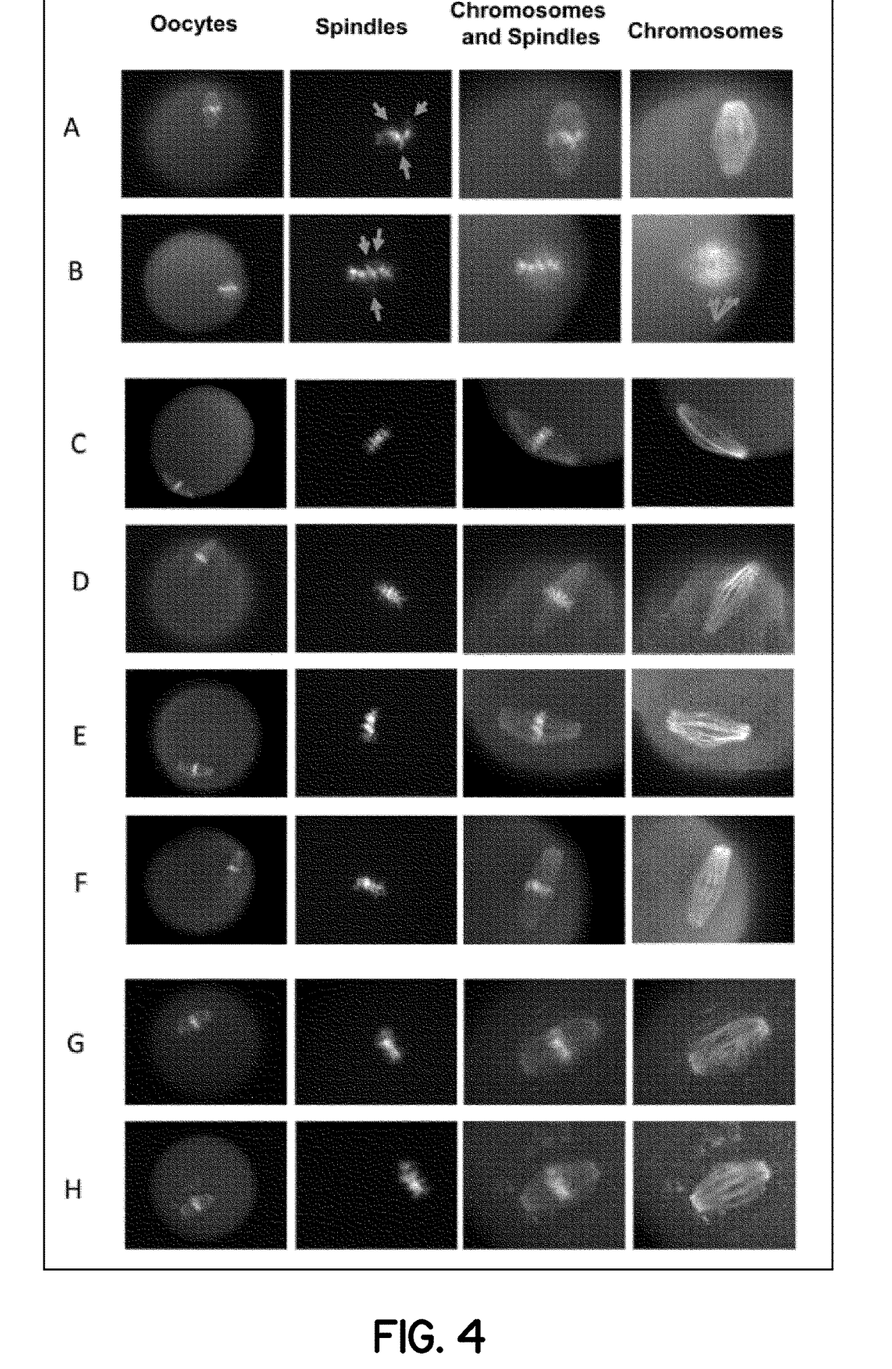
FIG. 4 is a series of photomicrographs of the effects of ActRIIB:Fc on chromosomes and spindles in ovulated oocytes from SAMP8 mice.
Figure 5:
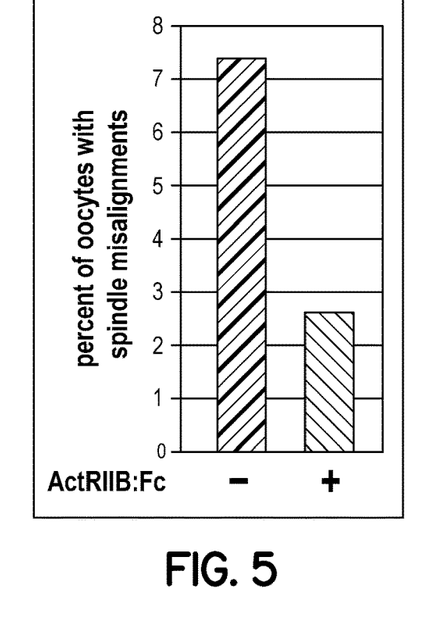
FIG. 5 is a graph of data demonstrating decrease in spindle misalignments in oocytes from SAMP8 mice treated with ActRIIB:Fc.

Midlife SAMP8 mice have elevated FSH compared to young SAMP8 mice. Chromosome misalignments and spindle aberrations are highly predictive of impending aneuploidy. If chronic elevation of FSH increases the rates of oocyte chromosome misalignments and spindle aberrations in midlife mice, then the treatment of midlife mice for the duration of oocyte growth with the FSH-lowering agent ActRIIB:Fc (about 3 estrous cycles) would be expected to decrease the rates of chromosome misalignments and spindle aberrations in freshly ovulated oocytes. Freshly ovulated oocytes from SAMP8 mice were stained to visualize chromosomes and spindles and examined in immunofluorescence microscopy (FIG. 4). Each individual oocyte was scored as having either well-aligned or misaligned meiotic chromosomes and spindles, according to methods described. Treatment of midlife mice with ActRIIB:Fc at a dose of 7 mg/kg for 19-24 days significantly decreased the rate of chromosome misalignments, from 31/193 (16.1%) in the untreated mice, to 11/159 (6.9%) in the ActRIIB:Fc-treated mice (P=0.0060), a 2.33-fold suppression (FIGS. 4 and 5). The fraction of oocytes from ActRIIB:Fc-treated mice that had with misaligned chromosomes was also significantly lower than that which was observed in the young mice, who had 26/210 (12.4%; P=0.0200). These data demonstrate that ActRIIB:Fc lowers the rate of oocyte chromosome misalignments below that of both midlife and young SAMP8 mice.

The frequency of spindle aberrations in SAMP8 oocytes significantly increases with age. 1/195 (0.51%) oocytes from young SAMP8 exhibit spindle aberrations, vs. 14/188 (7.4%) of oocytes from midlife SAMP8 mice, a 14.5-fold increase (P=0.0003). The rate of spindle aberrations in oocytes from midlife SAMP8 mice is significantly decreased by ActRIIB:Fc treatment, to 4/152 (2.63%), a 2.8-fold decrease (P=0.0200). The rate of spindle aberrations in the oocytes of midlife mice after ActRIIB:Fc treatment is statistically indistinguishable from that of the young mice (P=0.1179, NS). ActRIIB:Fc thus restores the rate of spindle aberrations in midlife SAMP8 mice to that of young SAMP8 mice.

FIG. 4 demonstrates that treatment of midlife SAMP8 mice with ActRIIB:Fc for 19-24 days restores organization of chromosomes and spindles in ovulated oocytes. Regularly cycling mice were injected with hCG on the afternoon of proestrus after 19-24 days of ActRIIB:Fc treatment to trigger ovulation. Freshly ovulated oocytes were recovered from ovarian ampullae on the morning of estrus. Oocytes were fixed, stained, and examined in fluorescence microscopy. A and B: Oocytes from midlife SAMP8 mice. C, D, E and F: Oocytes from midlife SAMP8 mice treated with ActRIIB:Fc. G and H: Oocytes from untreated young mice.

FIG. 5 demonstrates that treatment of midlife SAMP8 female mice with ActRIIB:Fc significantly reduces the incidence of chromosome misalignments in ovulated oocytes. Chromosome misalignments were scored in individual oocytes examined in fluorescence microscopy. Fraction and percentage of oocytes with misaligned chromosomes is significantly lower in mice treated with ActRIIB:Fc. P value was calculated with a Fisher exact test. In midlife SAMP8 female mice 14 of 188 oocytes (7/4%) had spindle aberrations. In SAMP8 mice treated with ActRIIB:Fc, only 4 of 152 oocytes had spindle aberrations. ActRIIB:Fc resulted in a significant (P=0.02) 2.8 fold reduction in oocytes with spindle aberrations.

The data further demonstrate that treatment of midlife SAMP8 female mice with ActRIIB:Fc significantly reduces the incidence of spindle aberrations in ovulated oocytes.

ActRIIB:Fc improves fertility lost with age in SAMP8 female mice. SAMP8 female mice display a significant decline in litter sizes with age, from a mean of 8.22 pup per litter at the age of 3-4 months, to a mean of 5.06 pups/litter by the age of 5.8 months (P<0.0001). The median number of pups per litter also decreased from 9 per litter in young SAMP8 to 5 per litter in midlife SAMP8. Regular estrous cyclicity is observed in both age groups.

Treating midlife mice with ActRIIB:Fc restores some of the fertility that is lost with age. Three weeks of treatment of midlife female SAMP8 mice with ActRIIB:Fc significantly increased the fertility of midlife SAMP8 mice. Litter sizes increased to a mean of 6.3 pups/litter and a median of 7 pups per litter, a 39-50% recovery of litter size (P=0.0306).

Figure 6:
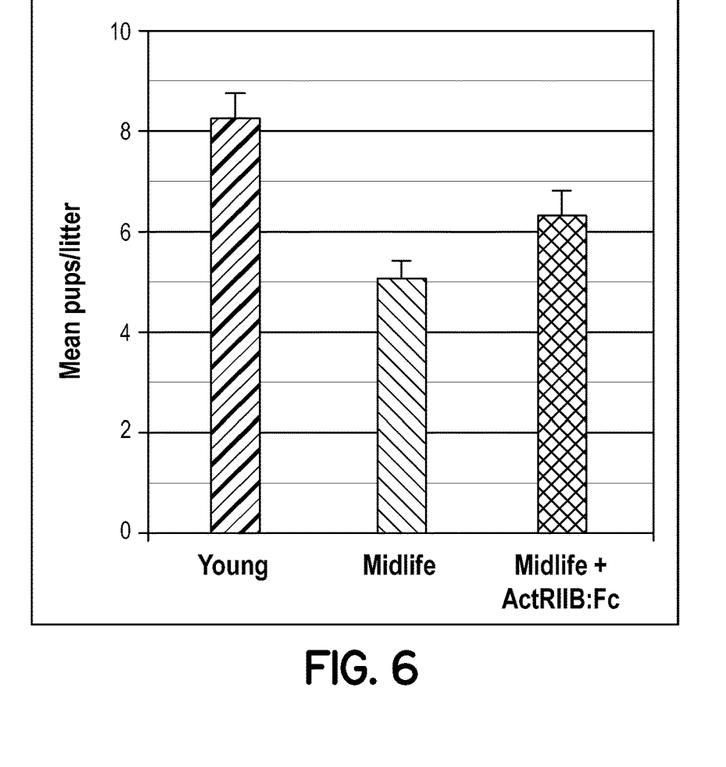
FIG. 6 is a graph of data demonstrating the effect of ActRIIB:Fc on litter size in midlife SAMP8 mice.

FIG. 6 demonstrates that ActRIIB:Fc increases the fertility of midlife SAMP8 mice. Midlife SAMP8 female mice were treated for 3 weeks with ActRIIB:Fc and then mated with young SAMP8 males. Control young and midlife mice were untreated prior to mating with young males. Number of pups per litter was counted in each test group, Mating plugs in SAMP8 mice are difficult to discern, so the mice that mated could not be definitively distinguished from those that had not mated. Therefore, dams that had no litters were excluded from the dataset. P value was calculated with a Mann-Whitney test. Young SAMP8 mice (3-4 months) had an average litter size of 8.22 pups (N=27 litters, Median 9 pups/litter). Midlife untreated SAMP8 mice (5.8 months) had an average litter size of 5.061 pups (N=33 litters, Median=5 pups/litter). Midlife SAMP8 mice treated with ActRIIFB:Fc had an average litter size of 6.294 pups (N=17 litters, Median+7). The P valve for the midlife untreated and the midlife treated was 0.0306.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:
1. A method of treating and/or reducing the incidence of infertility, miscarriages, trisomic pregnancies, or birth defects in a female subject, wherein said infertility, miscarriages, trisomic pregnancies, or birth defects result from oocyte aneuploidy, embryonic aneuploidy, and/or fetal aneuploidy, said method comprising administering ActRIIB: Fc to a female subject at a dose sufficient to maintain serum levels of ActRIIB: Fc between 4 mg/kg and 10 mg/kg.

2. The method of claim 1 further comprising administering the ActRIIB: Fc for at least a portion of one reproductive cycle.

3. The method of claim 1 further comprising administering the ActRIIB: Fc for at least a portion of two or more reproductive cycles.

4. The method of claim 3 further comprising harvesting and/or attempting fertilization of an oocyte(s) after completion of the second reproductive cycle.

5. The method of claim 3 further comprising harvesting and/or attempting fertilization of an oocyte(s) after completion of at least the third reproductive cycle.

6. The method of claim 1 wherein the subject is one of a human subject or a non-human animal subject.

7. A method of increasing oocyte production in a female subject, said method comprising administering ActRIIB: Fc to a female subject at a dose sufficient to maintain serum levels of ActRIIB: Fc between 4 mg/kg and 10 mg/kg.

8. The method of claim 7 further comprising administering the ActRIIB: Fc for at least a portion of one reproductive cycle.

9. The method of claim 7 further comprising administering the ActRIIB: Fc for at least a portion of two or more reproductive cycles.

10. The method of claim 9 further comprising harvesting and/or attempting fertilization of an oocyte(s) after completion of the second reproductive cycle.

11. The method of claim 9 further comprising harvesting and/or attempting fertilization of an oocyte(s) after completion of at least the third reproductive cycle.

12. The method of claim 7 wherein the subject is one of a human subject or a non-human animal subject.

* * * * *